(12) United States Patent
Revel et al.

(10) Patent No.: US 8,394,367 B2
(45) Date of Patent: Mar. 12, 2013

(54) IL6R/IL6 CHIMERA FOR THERAPY OF CHEMOTHERAPY-INDUCED PERIPHERAL NEUROPATHY

(75) Inventors: Michel Revel, Rehovot (IL); Judith Chebath, Rehovot (IL); Hagit Krug, Bar Yam (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 1474 days.

(21) Appl. No.: 11/579,034

(22) PCT Filed: Apr. 28, 2005

(86) PCT No.: PCT/IL2005/000443
§ 371 (c)(1),
(2), (4) Date: Oct. 12, 2007

(87) PCT Pub. No.: WO2005/105134
PCT Pub. Date: Nov. 10, 2005

(65) Prior Publication Data
US 2011/0274647 A1    Nov. 10, 2011

(30) Foreign Application Priority Data
Apr. 29, 2004  (IL) .......................................... 161672

(51) Int. Cl.
*A61K 38/17* (2006.01)
*A61K 38/20* (2006.01)
*A61K 48/00* (2006.01)

(52) U.S. Cl. ........................................ 424/85.2; 514/44
(58) Field of Classification Search .................. None
See application file for complete search history.

(56) References Cited

U.S. PATENT DOCUMENTS

| 7,531,644 | B2 | 5/1999 | Ekida et al. |
| 6,063,758 | A | 5/2000 | Lappi et al. |
| 6,706,261 | B1 * | 3/2004 | Ciliberto et al. ............. 424/85.2 |
| 7,374,912 | B2 | 5/2008 | Revel et al. |
| 2002/0058628 | A1 | 5/2002 | Noble et al. |

FOREIGN PATENT DOCUMENTS

| EP | 0504751 | 9/1992 |
| JP | 2001-509371 | 7/2001 |
| JP | 2003-502382 | 1/2003 |
| WO | 97/32891 | 9/1997 |
| WO | 99/02552 | 1/1999 |
| WO | 00/01731 | 1/2000 |
| WO | WO 00/78331 | 12/2000 |
| WO | 01/03737 | 1/2001 |
| WO | WO 03/033015 | 4/2003 |

OTHER PUBLICATIONS

Mikayama et al. Proc. Natl. Acad. Sci. USA, vol. 90, pp. 10056-10060 (1993).*
Voet et al. Biochemistry John Wiley & Sons, Inc., pp. 126-128 and 228-234 (1990).*
Flatters, et al., Abstract Only, "Nerve injury alters the effects of interleukin-6 on nociceptive transmission in peripheral afferents". *Eur. J. Pharmacol.*, vol. 484 (2-3), pp. 183-191, 2004.
Haggiag, et al., "Induction of myelin gene expression in Schwann cell cultures by an interleukin-6 receptor-interleukin-6 chimera", *FEBS Letters*, vol. 457, pp. 200-204, 1999.
Haggiag, et al., "Stimulation of Myelin Gene Expression In Vitro and of Sciatic Nerve Remyelination by Interleukin-6 Receptor-Interleukin-6 Chimera", *Journal of Neuroscience Research*, vol. 64, pp. 564-574, 2001.
Hayakawa, et al., "Nerve Growth Factor Prevents Neurotoxic Effects of Cisplatin, Vincristine and Taxol, on Adult Rat Sympathetic Ganglion Explants in Vitro", *Life Sciences*, vol. 55, No. 7, pp. 519-525, 1994.
Schafer, et al., "The IL-6/sIL-6R Fusion Protein Hyper-IL-6 Promotes Neurite Outgrowth and Neuron Survival in Cultured Enteric Neurons" *Journal of Interferon and Cytokine Research*, vol. 19, pp. 527-532, 1999.
Verstappen, et al., Abstract Only, "Neurotoxic Complications of Chemotherapy in Patients With Cancer: Clinical Signs and Optimal Management", *Drugs*, vol. 63, No. 15, pp. 1549-1563, 2003.
Boyle, et al., "Glutamate Ameliorates Experimental Vincristine Neuropathy", The Journal of Pharmacology and Experimental Therapeutics, 1996, pp. 410-415, vol. 279, No. 1.
Chebath, et al., "Interleukin-6 receptor-interleukin-6 fusion proteins with enhanced interleukin-6 type pleiotropic activities", Eur. Cytokine Netw., Dec. 1997, pp. 359-365, vol. 8, No. 4.
Corbi, et. al., Abstract, "Circulating soluble gp130, soluble IL-6R, and IL-6 in patients undergoing cardiac surgery, with or without extracorporeal circulation", Eur. J. Cardiotherac Surg., 2000, pp. 98-103, vol. 18(1).
Fischer, et al., "A bioactive designer cytokine for human hematopoietic progenitor cell expansion", Nature Biotechnology, Feb. 1997, pp. 142-145, vol. 15.
Mikayama, et al., "Molecular cloning and functional expression of a cDNA encoding glycosylation-inhibiting factor", Proc. Natl. Acad. Sci. USA, Nov. 1993, pp. 10056-10060, vol. 99.
Novick, et al., "Purification of soluble cytokine receptors from normal human urine by ligand-affinity and immunoaffinity chromatography", Journal of Chromatography, 1990, pp. 331-337, vol. 510.
Voet, et al., section 6-3: "Chemical Evolution", section 9-3 Abnormal Hemoglobins, Biochemistry, 1990, pp. 126-128 and 228-234.
Wang, et al., "Pathogenesis of Axonal Degeneration: Parallels Between Wallerian Degeneration and Vincristine Neuropathy", Journal of Neuropathology and Experimental Neurology, Jul. 2000, pp. 599-606, vol. 59, No. 7.
Windebank, et al., "Chemotherapy-induced neuropathy", Journal of the Peripheral Nervous System, 2008, pp. 27-46, vol. 13.
Yang, et al., "Human beta Cells Are Exceedingly Resistant to Streptozotocin in Vivo", Endocrinology, 2002, pp. 2491-2495, vol. 143(7).

* cited by examiner

*Primary Examiner* — Prema Mertz
(74) *Attorney, Agent, or Firm* — Browdy and Neimark, P.L.L.C.

(57) ABSTRACT

The invention relates to the use of IL-6R/IL-6 chimera in chemotherapy induced neuropathy.

61 Claims, 2 Drawing Sheets

IL6R/IL6 CHIMERA FOR THERAPY OF CHEMOTHERAPY-INDUCED PERIPHERAL NEUROPATHY

FIELD OF THE INVENTION

The present invention is in the field of chemotherapy-induced neuropathy. In particular, it relates to the use an IL-6R/IL-6 chimera for the treatment and/or prevention of chemotherapy induced neuropathy.

BACKGROUND OF THE INVENTION

Peripheral neuropathy is a complex of disorders of the peripheral nervous system resulting from damage to the nerve or to the myelin sheath. The damage is long lasting, usually outlasting the injury that initiates it.

Chemotherapy-induced peripheral neuropathy (CIPN) is a common and potential disabling side effect of many cytotoxic drugs. Chemotherapy-induced neuropathy is related to cumulative dose or dose-intensities (Verstappen et al. 2003 Drugs 63:1549-63).

The vinca-alkaloids (e.g. vincristine and vinblastine), platinum-based compounds (e.g. cisplatin) and taxanes (paclitaxel and docetaxel) are amongst the most important drugs inducing peripheral neurotoxicity (Visovsky C. Cancer Invest. 2003 June; 21(3): 439-51), Quasthoff S, Hartung H P J Neurol. 2002 January; 249(1): 9-17. Review). These drugs are widely used for treatment of various malignancies such as ovarian, breast cancer, and haematological cancers (Verstappen et al. 2003 Drugs 63(15): 1549).

Vincristine-driven neuropathy is mainly characterized by motor and sensory insufficiency (mixed type of neuropathy). Whilst the underlying mechanism is not fully understood as yet, it has been described to involve an alteration of anterograde axonal transport, ultimately leading to axonal degeneration. Up to now, treatment of vincristine-driven neuropathy is only palliative, as no efficient therapy has been developed so far.

Currently, CIPN is alleviated by dose reduction, which may compromise the efficacy of the chemotherapy treatment. Patients who already have neuropathic symptoms due to diabetes mellitus, hereditary neuropathies or early treatment with neurotoxic chemotherapy are thought to be more vulnerable for the development of CIPN.

In general, treatment of peripheral neuropathy is symptomatic and has no beneficial effect underlying damage to the nerves (Peltier A C, Russell J W. Recent advances in drug-induced neuropathies. Curr Opin Neurol. 2002 October; 15(5): 633-8). For example, pyridoxine (vitamin B6) is used as a method of nutritional support following peripheral nerve damage, antioxidants (e.g. gamma-linoleic acid, alphalipoic acid, and PKC inhibitors and aldose reductase inhibitors) are used to eliminate toxins which may contribute to peripheral neuropathy, anticonvulsant are used to suppress the pain symptoms. Attempts to prevent vincristine-neuropathy using putative neuroprotective agents such as vitamin B1, vitamin B12, glutamate (Boyle et al. J Pharmacol Exp Ther. 1996 October; 279(1): 410-5), isoaxonine (Le Quesne et al., J Neurol Neurosurg Psychiatry. 1985 September; 48(9): 933-5), gangliosides or nerve growth factor (Hayakawa et al., Life Sci. 1994; 55(7): 519-25. 4; Lewis et al. Exp Neurol. 1993 November; 124(1): 73-88) showed limited success.

Interleukin (IL)-6 is a pleiotropic cytokine that not only affects the immune system, but also acts in other biological systems and many physiological events in various organs. In a target cell, IL-6 can simultaneously generate functionally distinct or sometimes contradictory signals through its receptor complex, IL-6Ralpha and gp130. The final physiological output can be thought of as a consequence of the orchestration of the diverse signaling pathways generated by a given ligand. This concept, the signal orchestration model, may explain how IL-6 can elicit proinflammatory or anti-inflammatory effects, depending on the in vivo environmental circumstances. Elucidation of the molecular mechanisms underlying this issue is a challenging subject for future research (Jones et al. 2001, Heinrich et al. 2003 Biochem Journal 374, 1-20). The functional properties of IL-6 are extremely varied and this is reflected by the terminology originally used to describe this cytokine (Horst Ibelgaufts' COPE: Cytokines Online Pathfinder Encyclopaedia).

The biological activities of IL-6 are mediated by a membrane receptor system comprising two different proteins one named IL-6 Receptor (IL-6R or gp80 reviewed by Jones et al. FASEB J. 2001 January; 15(1): 43-58. Review) and the other gp130 (reviewed by Hirano et al Stem Cells. 1994 May; 12(3):262-77. Review). Soluble forms of IL-6R (sIL-6R), corresponding to the extracellular domain of gp80, are natural products of the human body found as glycoproteins in blood and in urine (Novick et al, J Chromatogr. 1990 Jun. 27; 510:331-7, and Cytokine. 1992 January; 4(1):6-11). An exceptional property of sIL-6R molecules is that they act as potent agonists of IL-6 on many cell types including human cells (Taga et al, Cell. 1989 Aug. 11; 58(3):573-81. Novick et al. 1992 January; 4(1):6-11). Even without the intracytoplasmic domain of gp80, sIL-6R is still capable of triggering the dimerization of gp130 in response to IL-6, which in turn mediates the subsequent IL-6-specific signal transduction and biological effects (Murakami Science. 1993 Jun. 18; 260(5115):1808-10). sIL-6R has two types of interaction with gp130 both of which are essential for the M-6 specific biological activities (Halimi et al., Eur Cytokine Netw. 1995 May-June; 6(3):135-43), and the active IL-6 receptor complex was proposed to be a hexameric structure formed by two gp130 chains, two IL-6R and two IL-6 ligands (Ward et al., 1994; Paonessa et al, EMBO J. 1995 May 1; 14(9):1942-51).

In contrast to the expression of the cognate IL-6R which has a limited cellular distribution (reviewed by Jones et al. 2001), expression of the trans-membrane-spanning gp130 is found in almost all organs, including heart, kidney, spleen, liver, lung, placenta, and brain (Saito et al J Immunol. 1992 Jun. 15; 148(12):4066-71).

In vitro, there are many different examples, which show that IL-6 alone does not induce a specific activity unless the soluble IL-6R is administered. For example, IL-6 induces osteoclast formation in co-cultures of mouse bone marrow and osteoblastic cells, only when combined with the sIL-6R (reviewed by Jones et al. 2001). Also, although many neuronal cells are capable of producing IL-6, they remain unresponsive to stimulation by IL-6 itself. Differentiation and survival of neuronal cells can, however, be mediated through the action of sIL-6R (Hirota J Exp Med. 1996 Jun. 1; 183(6): 2627-34, Martz 1998).

The circulating concentrations of sIL-6R (agonist) in normal subjects are relatively high and comparable to those of soluble gp130 of above 10 ng/ml, a natural antagonist of IL-6, (Corbi et al 2000 Eur J Cardiotherac Surg. 18 (1):98-103, Disthabanchong et al. Clin Nephrol. 2002 October; 58(4): 289-95). In contrast, the circulating concentrations of IL-6 are about or below 10 pg/ml (Kado et al. 1999 Acta Diabetol. Jun 36 (1-2)67-72, Corbi et al 2000. Thus the effect of IL-6 administration in vivo, alone, without co-administration with sIL-6R in disease may or may not be effective and depends on the concentration of the soluble agonist/antagonist in a particular disease and in a particular location in the body.

Chimeric molecules linking the soluble IL-6 receptor and IL-6 together have been described (Chebath et al. Eur Cytokine Netw. 1997 December; 8(4):359-65). They have been designated IL-6R/IL-6 chimera. The chimeric IL-6R/IL-6 molecules were generated by fusing the entire coding regions of the cDNAs encoding the soluble IL-6 receptor (sIL-6R) and IL-6. Recombinant IL-6R/IL-6 chimera was produced in CHO cells (Chebath et al, Eur Cytokine Netw. 1997, WO99/02552). The IL-6R/IL-6 binds with a higher efficiency to the gp130 chain in vitro than does the mixture of IL-6 with sIL-6R (Kollet et al, Blood. 1999 Aug. 1; 94(3):923-31).

MBP and P0 proteins are normally induced during the final postnatal maturation of Schwann cells, and they are re-induced during nerve regeneration. The IL-6R/IL-6 chimera has been shown to induce the expression of myelin basic protein (MBP) and P0 gene products MBP and P0 RNAs and proteins in cultures of dorsal root ganglia (DRG) from 14 day old mouse embryos (FEBS Lett. 1999 Aug. 27; 457(2):200-4. et al., 1999). In addition, the expression of MBP and P0 was found to be induced by IL6R/IL6 chimera also in cultured tumor cells of neural crest origin. In both cases, the induction of MBP and P0 genes by IL6R/IL6, chimera in normal embryonic Schwann cells precursors and in tumor cells of neural crest origin, is associated with a down-regulation of Pax-3 (Kamaraju et al JBC 2002 277 15132, Slutsky et al. J Biol Chem. 2003 Mar. 14; 278(11):8960-8, Haggiag et al, J. Neurosci. Res. 2001).

The stimulatory effect of the gp130 activator IL6R/IL6 on myelination in vivo was demonstrated in a rat model of sciatic nerve transection. Injections of IL6R/IL6 led to a 7-fold increase of the number of myelinated fibers in the regenerating nerve (Haggiag et al, J. Neurosci. Res. 2001).

The therapeutic effect of recombinant IL-6 alone without the soluble IL-6R in an animal model of diabetes-induced peripheral neuropathy has been disclosed in patent application WO03033015. However, it is uncertain whether IL6R/IL-6 chimera alone or IL-6 alone or together with sIL-6R, are capable of a beneficial effect in peripheral neuropathy caused by chemotherapy. In fact, recombinant leukemia inhibitor factor (LIF), another gp130 activator, was tested in clinical trials for preventing peripheral neuropathy caused by carboplatin/paclitaxel (Davis et al. Proc Am Soc Clin Oncol 22: page 740, 2003, abstr 2976) and the results indicated that LIF was ineffective at preventing CIPN at the doses and regime tested.

Therefore, new drugs/strategies for preventing/treating peripheral neuropathy caused by chemotherapy agents are thus needed.

SUMMARY OF THE INVENTION

The invention relates to the use of an IL6R/IL6 chimera, or a mutein, isoform, fused protein, functional derivative, circularly permutated derivative or a salt thereof, for the manufacture of a medicament for the prevention and/or treatment of Chemotherapy Induced Peripheral Neuropathy (CIPN).

The invention provides the use the IL6R/IL6 chimera of the invention in CIPN induced by chemotherapy agents such as cisplatin, dicarbazine, streptozocin, cyclophosphamide, carmustine, lomustine, procarbazine, mitomycin, cytarabine, methotrexate, 5-fluorouracil, vinblastine, vincristine, bleomycin, paclitaxel, asparaginase, busulfan, carboplatin, dacarbazine, fludarabine, hydroxyurea, ifosfamide, mercaptopurine, mitotane, streptozocin, taxol and or a mixture of two or more agents thereof and preferably by vincristine.

In one aspect of the invention, the IL6R/IL6 chimera can be glycosylated at one or more sites or non-glycosylated and/or the functional derivative may have at least one moiety, such as a polyethylene moiety, attached to one or more functional groups.

In addition, the invention provides a cell expressing IL6R/IL6 chimera to be used in the manufacture of a medicament for treatment and/or prevention of CIPN.

Also, the invention provides a vector, preferably a lentiviral vector, for expressing IL6R/IL6 chimera to be used in the manufacture of a medicament for treatment and/or prevention of CIPN.

In one embodiment, the invention provides a method for treating and/or preventing CIPN, comprising administering to a patient in need thereof a IL6R/IL6 chimera, or a mutein, isoform, fused protein, functional derivative, circularly permutated derivative or a salt thereof, optionally together with a pharmaceutically acceptable carrier.

In one aspect, the patient in need according to the invention may be a high risk patient such as patients suffering from diabetes, AIDS, hereditary neuropathies and patients subjected to early treatment with neurotoxic drugs.

In another aspect, the administration of the IL6R/IL6 chimera according to the invention can be intraliver, intradermal, intraplantar, transdermal, intramuscular, intraperitoneal, intravenous, subcutaneous, oral, epidural, topical, and intranasal routes.

In addition, the invention provides a method for increasing or prolonging the dose of a chemotherapeutic agent in a patient comprising administering to the patient in need thereof an IL6R/IL6 chimera, or a mutein, isoform, fused protein, functional derivative, circularly permutated derivative or a salt thereof, optionally together with a pharmaceutically acceptable carrier.

In another aspect of the invention, the IL6R/IL6 chimera may be administered either before during and/or after the chemotherapy agent.

In addition, the invention provides a pharmaceutical composition comprising a combination of IL6R/IL6 chimera, or an isoform, mutein, fused protein, or a functional derivative and a chemotherapeutic agent or a mixture of two or more agents thereof.

Chemotherapy agents in accordance with the invention may comprise cisplatin, dicarbazine, streptozocin, cyclophosphamide, carmustine, lomustine, procarbazine, mitomycin, cytarabine, methotrexate, 5-fluorouracil, vinblastine, vincristine, bleomycin, paclitaxel, asparaginase, busulfan, carboplatin, dacarbazine, fludarabine, hydroxyurea, ifosfamide, mercaptopurine, mitotane, streptozocin, taxol and or a mixture of two or more agents thereof and preferably vincristine.

In one embodiment of the invention, the pharmaceutical composition may further comprise additional drugs such as antioxidants, PKC inhibitors and neuroprotective agents and preferably, glutamate, pyridoxine, gamma-linoleic acid, vitamin B1, vitamin B2, isoaxonine, ganglioside and NGF.

(A) Outgrowing axonal network stained for βIII-tubulin in DRG cultures after 16 days in NGF-containing medium. (B) Similar culture supplemented with 200 ng/ml IL-6R/IL-6 from day 5 to 16. (C) Culture as in A, treated with 5 nM vincristine from day 5 to 10. After removal of the drug, the culture was continued for 6 more days. (D) Culture as in A, treated with 5 nM vincristine from day 5 to 10, and then with IL-6R/IL-6 for 6 more days following the removal of the drug. (E) DRG culture as in C, with vincristine from day 5 to 10, and further culture 6 days without the drug. Outgrowth stained for GFAP. (F) Culture as in D, with vincristine from day 5 to 10, and further culture 6 days with IL-6R/IL-6. Note the regrowth of GFAP positive cells. Panels A-D and E-F are at the same magnification respectively; size bar: 100 µm.

DETAILED DESCRIPTION OF THE INVENTION

The invention relates to the use of an IL6R/IL6 chimera, or a mutein, isoform, fused protein, functional derivative or circularly permutated derivative or a salt thereof, for the manufacture of a medicament for the prevention of Chemotherapy Induced Peripheral Neuropathy (CIPN).

Currently, treatment of peripheral neuropathy is symptomatic and has no beneficial effect underlying damage to the nerves. Typically, CIPN is alleviated by dose reduction, which may compromise the efficacy of treatment.

Thus, the present invention presents a substantial progress, namely, IL6R/IL6 chimera can be used together with the chemotherapeutic agent to prevent chemotherapy-induced damage development. Moreover, it was shown that IL6R/IL6 chimera administered in vitro after development of chemotherapy-induced damage was able to restore neural tissue.

Therefore, the invention relates to the treatment and/or prevention of CIPN caused by a wide range of chemotherapy agents selected from vinca-alkaloids (e.g. vincristine and vinblastine), platinum-based compounds (e.g. cisplatin) and taxanes (paclitaxel and docetaxel) or a combination of more than one agent thereof, by administration of IL6R/IL6 chimera.

The invention is based on the findings that co-administration of IL6R/IL6 chimera with vincristine was very efficient at preventing induction of axonal degeneration by vincristine in vitro.

Figure 1:
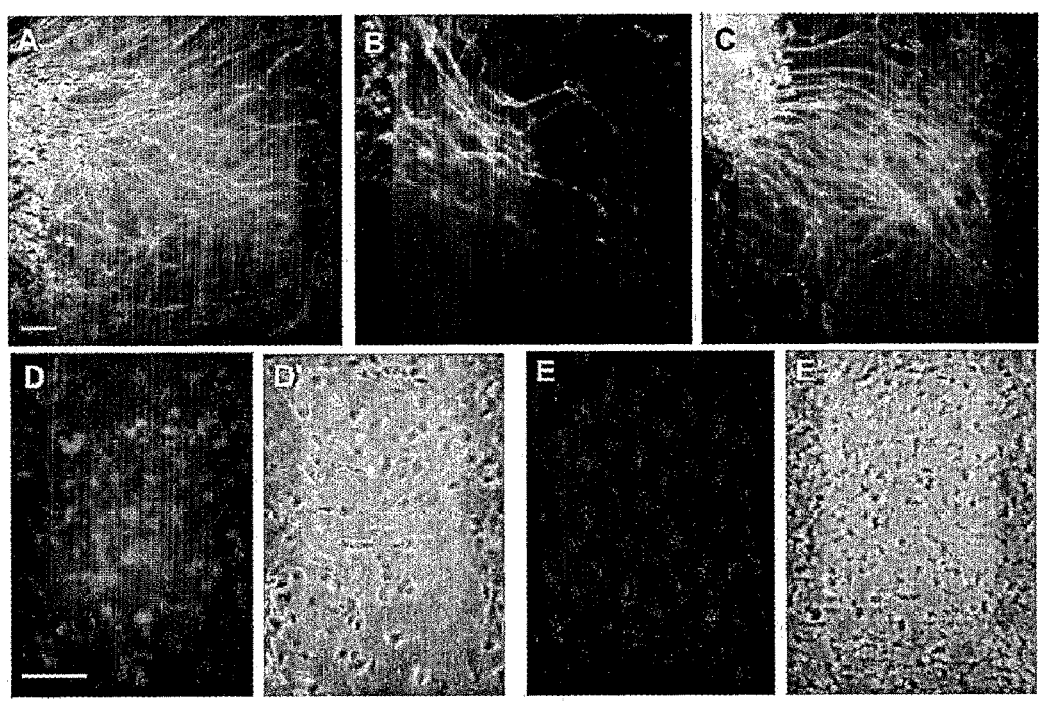
FIG. 1 shows in vitro neuroprotection against vincristine by activation of IL-6 signaling. (A) Outgrowing axonal network stained for βIII-tubulin in DRG cultures after 7 days in NGF-containing medium. (B) Similar culture treated for the last 2 days with 10 nM vincristine. Note the extensive neurodegeneration. (C) Similar culture treated for the last 2 days with vincristine and 200 ng/ml IL-6R/IL-6. Significant protection of the axonal network is observed. Panels A-C are at same magnification; size bar: 100 µm. (D) Outgrowth of DRG cultured in NGF-containing medium for 10 days, with 10 nM vincristine added for the last 5 days. Cells undergoing apoptosis are visualized by staining with antibodies against activated caspase-3. (E) Similar culture in which 200 ng/ml IL-6R/IL-6 was added together with vincristine. No apoptosis is observed. (D', E') same fields as D, E under light phase contrast. Panels D-E' at same magnification; size bar: 100 µm.

For example, neuronal outgrowth was stimulated in cultures of dorsal root ganglia (DRG) from mouse embryos (day E17) by addition of Nerve Growth Factor (NGF). Subsequently the cultures were exposed to vincristine, which induces a progressive axonal degeneration process due to caspase-3 activation. After 2 days of vincristine treatment caspase-3 activation and a considerable loss of axons in the DRG neuronal outgrowth and were observed (FIG. 1, panels B versus A and D). However, unexpectedly, when IL-6R/IL-6 was present during the vincristine treatment there was virtually no caspase-3 activation (FIG. 1, panels E versus D). It was also observed that IL-6R/IL-6 prevented axonal degeneration (FIG. 1, panels C versus B).

The invention is based also on the findings that the treatment with IL6R/IL6 chimera efficiently restored neural tissue even if added after the neural damage by vincristine was already established.

Figure 2:
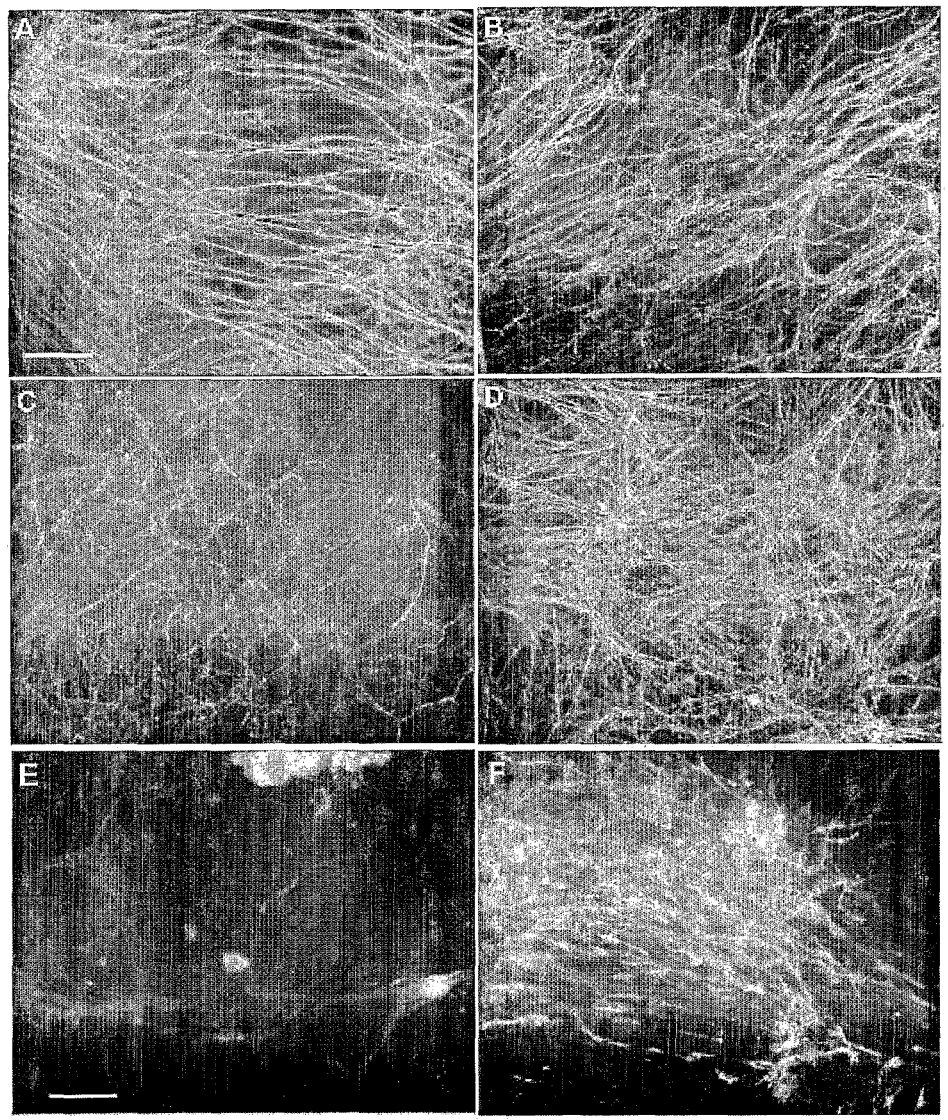
FIG. 2 shows stimulation of regeneration following vincristine intoxication.

For example, DRG of E18.5 embryos from IL-6 deficient mice (IL-6−/−) cultures in which the axonal network was formed in the presence of NGF for 5 days were either continued for another 11 days without or with IL-6R/IL-6 (FIG. 2, panel A and B, respectively), or treated for 5 days by vincristine at which time vincristine was removed and culture continued for 6 more days (FIG. 2, panels C-F). It was observed that the extensive degeneration of the axonal network was still present 6 days after vincristine was removed (FIG. 2, panel C) but when IL-6R/IL-6 was added after vincristine removal a significant re-growth of the axons was observed (FIG. 2, panel D). In parallel cultures immunostained for glial fibrillary acidic protein-(GFAP), the addition of IL-6R/IL-6 was seen to produce a marked re-growth of glial cells (FIG. 2, panel F) as compared to the control cultures 6 days after vincristine removal (FIG. 2, panel E).

In several similar experiments, the Curative effects of IL-6R/IL-6 were seen in DRG cultures from IL-6+/+ mice, and were apparent already two days after IL-6R/IL-6 addition (not shown).

Altogether, the results obtained unequivocally demonstrate the preventive and/or curative therapeutic value of IL6R/IL6 in CIPN.

The IL6R/IL6 chimera, or a mutein, isoform, fused protein, functional derivative, or circularly permutated derivative or a salt thereof, according to the invention, can be for example non-glycosylated or can be glycosylated at one or more sites.

In a preferred embodiment, the functional derivative may comprise at least one moiety, such as a polyethylene moiety, attached to one or more functional groups, which occur as one or more side chains on the amino acid residues.

In another embodiment, IL-6R/IL-6 chimera according to the invention, may be administered by a cell expressing IL6R/IL6 chimera, or a mutein, isoform, fused protein, or circularly permutated derivative thereof or by an expression vector comprising the coding sequence of an IL6R/IL6 chimera, or a mutein, isoform, fused protein, or circularly permutated derivative thereof. In a preferred embodiment, the vector is a lentiviral vector.

The invention relates also to a method for treating and/or preventing CIPN, comprising administering to a patient in need thereof IL6R/IL6 chimera, or a mutein, isoform, fused protein, functional derivative, circularly permutated derivative or a salt thereof, optionally together with a pharmaceutically acceptable carrier.

In a preferred embodiment, the patient in need is a high risk patient, such as those patients having suffered from diabetes mellitus already for a prolonged period of time, patients who already have neuropathic symptoms due to AIDS and, patients with hereditary neuropathies or subjected to early treatment with neurotoxic chemotherapy etc.

The invention relates also to a method for increasing the dose of a chemotherapeutic agent to a patient in need thereof comprising administering a IL6R/IL6 chimera, or a mutein, isoform, fused protein, functional derivative, circularly permutated derivative or a salt thereof, optionally together with a pharmaceutically acceptable carrier prior after or during the chemotherapeutic agent. The chemotherapeutic agent according to the invention may be selected from agents such as cisplatin, dicarbazine, streptozocin, cyclophosphamide, carmustine, lomustine, procarbazine, mitomycin, cytarabine, methotrexate, 5-fluorouracil, vinblastine, vincristine, bleomycin, paclitaxel, asparaginase, busulfan, carboplatin, dacarbazine, fludarabine, hydroxyurea, ifosfamide, mercaptopurine, mitotane, streptozocin, taxol and or a mixture of two or more agents thereof.

In addition, the invention relates to a pharmaceutical composition comprising a combination of IL6R/IL6 chimera, or an isoform, mutein, fused protein, functional derivative or fragment thereof, and a chemotherapeutic agent. More specifically, in the pharmaceutical composition according to the invention the chemotherapy agents is selected from cisplatin, dicarbazine, streptozocin, cyclophosphamide, carmustine, lomustine, procarbazine, mitomycin, cytarabine, methotrexate, 5-fluorouracil, vinblastine, vincristine, bleomycin, paclitaxel, asparaginase, busulfan, carboplatin, dacarbazine, fludarabine, hydroxyurea, ifosfamide, mercaptopurine, mitotane, streptozocin, taxol and or a mixture of two or more agents thereof.

In one embodiment a preferred chemotherapeutic agent was vincristine.

In a more preferred embodiment, the pharmaceutical composition further comprises a an additional drug such as for example, pyridoxine (vitamin B6), antioxidants (e.g. gammalinoleic acid, alphalipoic acid, PKC inhibitors and aldose reductase inhibitors, anticonvulsant are used to suppress the pain symptoms, neuroprotective agents such as vitamin B1, vitamin B12, glutamate (Boyle et al., 1996), isoaxonine (Le Quesne et al., 1985), gangliosides or nerve growth factor.

An "IL-6R/IL-6 chimera" (also called "IL-6R/IL-6" or "IL-6 chimera"), as used herein, is a chimeric molecule comprising a soluble part of gp130 fused to all or a biologically active fraction of interleukin-6. The moieties of the chimeric protein can be fused directly to one another, or they can be linked by any suitable linker, such as a disulfide bridge or a polypeptide linker. The linker may be a short linker peptide which can be as short as 1 to 3 amino acid residues in length or longer, for example, 13 or 18 amino acid residues in length. Said linker may be a tripeptide of the sequence E-F-M (Glu-Phe-Met) (amino acids 338-40 of SEQ ID NO:3) for example, or a 13-amino acid linker sequence comprising Glu-Phe-Gly-Ala-Gly-Leu-Val-Leu-Gly-Gly-Gln-Phe-Met (SEQ ID NO:6) introduced between the amino acid sequence of the soluble IL-6 receptor gp130 and the IL-6 sequence. Examples of IL-6R/IL-6 chimera are known in the art and have been described in detail e.g. in WO 99/02552 (which discloses the instant SEQ ID NO: 6 and 7) or WO 97/32891 (disclosing RGGGGSGGGGSVE, SEQ ID NO:8; cp. amino acids 212-224 of SEQ ID NO:4); in Fischer (1997) (also disclosing SEQ ID NO:8); and in Ekida, WO 00/01731. In Ekida, the explicitly disclosed linkers are proline (P), "G2" (Gly-Gly), "G4" (Gly-Gly-Gly-Gly, amino acids 1-4 of SEQ ID NO:9), "G4S" (GGGGS, amino acids 1-5 of SEQ ID NO:9); and "G4S2" (GGGGSGGGGS, amino acids 1-10 of SEQ ID NO:9); and "G4S3" (SEQ ID NO:9).

The terms "treating/curing and preventing" as used herein should be understood as preventing, inhibiting, attenuating, ameliorating or reversing one or more symptoms or cause(s) of chemotherapy neuropathy, as well as symptoms, diseases or complications accompanying chemotherapy neuropathy. When "treating/curing" chemotherapy neuropathy, the substances according to the invention are given after onset of the disease, "prevention" relates to administration of the substances before any signs of disease can be noted in the patient.

The term "chemotherapy neuropathy" relates to any form of chemotherapy neuropathy, or to one or more symptom(s) or disorder(s) accompanying or caused by chemotherapy neuropathy, or complications of chemotherapy affecting nerves as described in detail in the introduction above.

The term "dose" relates to the quantity to be administered at one time, such as a specified amount of medication.

The term "dosage" relates to the determination and regulation of the size, frequency, and number of doses.

As used herein the term "muteins" refers to analogs of an IL6R/IL6 chimera, in which one or more of the amino acid residues of the naturally occurring components of IL6R/IL6 chimera are replaced by different amino acid residues, or are deleted, or one or more amino acid residues are added to the original sequence of an IL6R/IL6 chimera, without changing considerably the activity of the resulting products as compared with the original IL6R/IL6 chimera. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes an IL6R/IL6 chimera, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of an IL6R/IL6 chimera, such as to have substantially similar, or even better, activity to IL6R/IL6 chimera.

Characteristic activity of IL6R/IL6 chimera is the capability of binding to the gp130. As long as the mutein has substantial capability of binding to gp 130 it can be considered to have substantially similar activity to IL6R/IL6 chimera. Thus, it can be determined whether any given mutein has at least substantially the same activity as IL6R/IL6 chimera by means of routine experimentation comprising subjecting hepatocytes to such mutein, and to determine whether or not it induces hepatocyte proliferation e.g. by measuring BrdU or labelled methionine uptake or just by counting the cells the cells vis-à-vis non treated control cells and cells treated with WT IL6R/IL6 chimera. An ELISA type assay for measuring the binding of IL-6R/IL-6 chimera to gp130 has been described in detail in example 7 on page 39 of WO 99/02552.

A microliter 96-well plate (Nunc) is coated with anti-human gp130 monoclonal antibody and 50 ng/ml of gp13O (both from R & D Systems, Minneapolis) is added. After washing in phosphate buffered saline, the IL-6R/IL-6 chimera is added in different wells at different concentrations ranging from 0.1 to 50 ng/ml. After incubation overnight at 40 C, a rabbit polyclonal anti-IL-6R (Oh et al., Cytokine, 8, 401-409, 1996) is added, followed by goat antirabbit Ig conjugated with horseradish peroxidase, which is detected by colored reaction (Sigma, St. Louis).

As long as the mutant has substantial binding activity to gp130 it can be considered to have substantially similar activity to IL-6R/IL-6.

Thus it can be determined whether any given mutant has at least substantially the same activity as IL-6R/IL-6 chimera by means of routine experimentation comprising subjecting such mutant e.g. to a simple sandwich binding assay to determine whether or not it binds to an immobilized gp130 or soluble gp130 (extracellular fragment of gp130) as described in example 7 of WO 99/02552.

In a preferred embodiment, any such mutein has at least 40% identity or homology with the sequence of mature IL-6R/IL-6 chimera. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Muteins of IL-6R/IL-6 chimera, which can be used in accordance with the present invention, or nucleic acid coding therefore, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of IL-6R/IL-6 chimera may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table A. More preferably, the synonymous amino acid groups are those defined in Table B; and most preferably the synonymous amino acid groups are those defined in Table C.

TABLE A

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE B

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE C

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |

TABLE C-continued

Most Preferred Groups of Synonymous Amino Acids

| Amino Acid | Synonymous Group |
|---|---|
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-6 polypeptides, for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al).

The term "fused protein" refers to a polypeptide comprising an IL-6R/IL-6 chimera, or a mutein or fragment thereof, fused with another protein, which, e.g., has an extended residence time in body fluids. An IL-6R/IL-6 chimera may thus be fused to another protein, polypeptide or the like, e.g., an immunoglobulin or a fragment thereof.

"Functional derivatives" as used herein cover derivatives of IL-6R/IL-6 chimera, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-6R/IL-6 chimera, and do not confer toxic properties on compositions containing it.

These derivatives may, for example, include polyethylene glycol side-chains, which may mask antigenic sites and extend the residence of an IL-6R/IL-6 chimera in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

The term "salts" herein refers to both salts of carboxyl groups and to acid addition salts of amino groups of the IL-6R/IL-6 chimera molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of IL-6R/IL-6 chimera, e.g. the ability to prevent or ameliorate CIPN and/or the ability to bind gp130.

"Isoforms" of IL-6R/IL-6 chimera are proteins capable of binding gp130 or fragment thereof, which may be produced by alternative splicing.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

The IL-6 chimera may be selected from that described by Chebath et al. (Eur Cytokine Netw. 1997 December; 8(4): 359-65. 1997), Hyper-intyerleukin-6 by Fischer et al. (Fischer et al. Nat Biotechnol. 1997 February; 15(2):142-5) and the fused protein with direct bond of IL-6-receptor to IL-6 by Eldda Teiji, Ide Teruhiko (WO0001731).

In a preferred embodiment of the invention, the IL-6 chimera is glycosylated at one or more sites.

A glycosylated form of an IL6R/IL6 chimera has been described in WO 99/02552 (PCT/IL98/00321), which is the chimeric molecule highly preferred according to the invention. The IL6R/IL6 chimera described therein is a recombinant glycoprotein, which was obtained fusing the entire coding sequence of the naturally occurring soluble IL-6 receptor δ-Val (Novick et al., J Chromatogr. 1990 Jun. 27; 510:331-7) to the entire coding sequence of mature naturally occurring IL-6, both from human origin.

The IL-6R/IL-6 chimera according to the invention may be produced in any adequate eukaryotic or procaryotic cell type, like yeast cells, insect cells, bacteria, and the like. It is preferably produced in mammalian cells, most preferably in genetically engineered CHO cells as described in WO 99/02552.

In a further embodiment of the invention, the substance of the invention is not glycosylated. Advantageously, the molecule can then be produced in bacterial cells, which are not capable of synthesizing glycosyl residues, but usually have a high yield of produced recombinant protein. The production of non-glycosylated IL-6R/IL-6 chimera can be done, for example, in bacteria as described for the production of non-glycosylated IL-6 which has been described in detail in EP504751B1.

In yet a further embodiment, the substance according to the invention comprises an immunoglobulin fusion, i.e. the molecules according to the invention are fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of the IL-6R/IL-6 chimera. The resulting fusion protein ideally has improved properties, such as an extended residence time in body fluids (half-life), increased specific activity, increased expression level, or facilitated purification of the fusion protein.

Preferably, the substance according to the invention is fused to the constant region of an Ig molecule. It may be fused to heavy chain regions, like the CH2 and CH3 domains of human IgG1, for example. Other isoforms of Ig molecules are also suitable for the generation of fusion proteins according to the present invention, such as iso forms IgG$_2$ or IgG$_4$, or other Ig classes, like IgM or IgA, for example. Fusion proteins may be monomeric or multimeric, hetero- or homomultimeric.

Functional derivatives of the substance according to the invention may be conjugated to polymers in order to improve the properties of the protein, such as the stability, half-life, bioavailability, tolerance by the human body, or immunogenicity.

Therefore, a preferred embodiment of the invention relates to a functional derivative of the substance according to the invention comprising at least one moiety attached to one or more functional groups, which occur as one or more side chains on the amino acid residues.

A highly preferred embodiment relates to a substance of the invention linked to polyethylene glycol (PEG). PEGylation may be carried out by known methods, such as the ones described in WO 92/13095, for example.

The definition of "pharmaceutically acceptable" is meant to encompass any carrier, which does not interfere with effectiveness of the biological activity of the active ingredient and that is not toxic to the host to which it is administered. For example, for parenteral administration, IL-6R/IL-6 chimera may be formulated in a unit dosage form for injection in vehicles such as saline, dextrose solution, serum albumin and Ringer's solution.

The IL-6R/IL-6 chimera can be administered to a patient in need of administration thereof in a variety of ways. The routes of administration can be intraliver, intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule encoding the IL-6R/IL-6 chimera is administered to the patient (e.g. via a vector), which causes the IL-6R/IL-6 chimera to be expressed and secreted in vivo. In addition the IL-6R/IL-6 chimera can be administered together with other components of biologically active agents such as pharmaceutically acceptable surfactants, excipients, carriers, diluents and vehicles.

For parenteral (e.g. intravenous, subcutaneous, intramuscular) administration, IL-6R/IL-6 chimera can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

It is a further object of the present invention to provide for a method for treating and/or preventing CIPN, comprising administering to a patient in need thereof an effective amount/dose of IL-6R/IL-6 chimera, a mutein, fused protein, functional derivative, circularly permutated-derivative or salt thereof optionally together with a pharmaceutically acceptable carrier.

An "effective amount" refers to an amount of the active ingredients that is sufficient to affect the course and the severity of the diseases described above, leading to the reduction or remission of such pathology. The effective amount will depend on the route of administration and the condition of the patient.

The dosage administered, as single or multiple doses, to an individual will vary depending upon a variety of factor, including IL-6R/IL-6 chimera pharmacokinetic properties, the route of administration, patient conditions and characteristics (sex, age, body weight, health, size), extent of symptoms, concurrent treatments, frequency of treatment and the effect desired. Adjustment and manipulation of established, dosage ranges are well within the ability of those skilled.

The invention relates to the use an IL-6R/IL-6 chimera or a mutein, fused protein, or circularly permutated derivative in the manufacture of a medicament for the treatment and/or prevention of CIPN.

The dose of IL-6R/IL-6 chimera can be administered before during and/or after chemotherapy. The dose of IL-6R/IL-6 chimera can be administered prophylacticaly before CIPN is established or for treating established CIPN.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

The present invention will now be described in more detail in the following non-limiting examples and the accompanying drawings.

EXAMPLES

Example 1

In Vitro Effects of IL-6R/IL-6 Chimera on Dorsal Root Ganglia Cells Intoxicated by Vincristine IL-6R/IL-6 chimera (Chebath et al, 1997) was used to explore prevention against vincristine intoxication in vitro.

For this purpose, cultures of dorsal root ganglia (DRG) from mouse embryos (day E17) in which neuronal outgrowth was stimulated by Nerve Growth Factor (NGF), were subsequently exposed to 10 nM vincristine which induces a progressive axonal degeneration process (Wang et al., J Neuropathol Exp Neurol. 2000 July; 59(7):599-606). After 2 days, a considerable loss of axons in the DRG outgrowth was evident after immunostaining for βIII-tubulin (FIG. 1, panels B versus A). Addition of IL-6R/IL-6 during the treatment by vincristine prevented axonal degeneration (panel C). Neurodegeneration was further examined by monitoring the proteolytic activation of caspase-3, which denotes the early stages of apoptosis in various neuropathies (Russell et al, Neurobiol Dis. 1999 October; 6(5):347-63). Positive reaction to antibodies against activated caspase-3 was observed in the DRG cultures treated for 5 days with vincristine (panel D). However, when IL-6R/IL-6 was present during the vincristine treatment there was virtually no caspase-3 activation (panel E).

Example 2

In Vitro Effects of IL-6R/IL-6 Chimera on Dorsal Root Ganglia Cells Intoxicated by Vincristine I further investigated whether the IL-6R/IL-6 could have neural regenerative effects by adding IL-6R/IL-6 after the action of vincristine had taken place. One such experiment carried out with DRG of E18.5 embryos from IL-6 deficient mice (IL-6−/−) is shown in FIG. 2. Cultures in which the axonal network was formed in the presence of NGF for 5 days were either continued for another 11 days without or with IL-6R/IL-6 (Panel A and B, respectively), or treated for 5 days by vincristine at which time vincristine was removed and culture continued for 6 more days (panels C-F). The extensive degeneration of the axonal network was still observed 6 days after vincristine was removed (panel) but when IL-6R/IL-6 was added, after vincristine removal, a significant re-growth of the axons was observed (panel D). In parallel in cultures immunostained for glial fibrillary acidic protein (GFAP), the addition of IL-6R/Il-6 was found to produce a marked re-growth of glial cells (panel F) as compared to the control cultures 6 days after vincristine removal (panel E). In several similar experiments, the neural regenerative effects of IL-6R/Il-6 were seen in DRG cultures from IL-6+/+ mice, and were apparent already two days after IL-6R/IL-6 addition (not shown). These experiments indicate that IL-6R/IL-6 chimera promotes regeneration of neural and glial cells when added after exposure to the chemotherapeutic agent.

Example 3

Dorsal Root Ganglia (DRG) Cultures, Vincristine and IL-6R/IL-6 Treatments

DRGs were prepared as detailed before (Haggiag et al, 1999, 2001) from embryos of (C57BL/6×129Sv) F1 mice. In some experiments, corresponding IL-6−/− mutant mice were used (Mendel et al, 1998). The DRGs were seeded onto glass coverslips (precoated with a solution of 20 µg/ml poly-D-lysine, 250 µg/ml fibronectin), which were placed in 12-well Costar plates. The regular culture medium was 0.5 ml DMEM/F12 medium with 1% N2 supplement, 10% fetal bovine serum, 2% horse serum, 1.4 mM glutamine (all from Gibco/Invitrogen) and 50 ng/ml NGF (2.5S; Alomone Labs, Jerusalem, Israel). Cultures were maintained at 37° C., 5% $CO_2$ and medium replaced every third day. On day 5, some of the wells were supplemented with 10 nM vincristine sulfate salt (Sigma, St Louis, Mo.), or vincristine together with 200 ng/ml pure recombinant IL-6R/IL-6, prepared as described (Chebath et al, 1997). After 2-5 days, the cultures were fixed in 4% paraformaldehyde, 10 minutes at room temperature (RT), washed in PBS, then treated with 0.5% Triton X-100 and 10% normal goat serum in PBS for 3 minutes at RT and washed 3 times with 1% NGS. For studying the curative effects, similar DRG cell cultures treated on day 5 with vincristine (5 nM) were washed on day 10 to remove vincristine and replenished with the above regular medium either alone or supplemented with 200 ng/ml IL-6R/IL-6 and culture continued for 6 more days before fixation.

Example 4

Immunostaining

Immunostaining was overnight at RT with mouse monoclonal antibody TUJ1 anti-neuronal βIII-tubulin antibody (Covance, Berkeley, Calif.; MMS-435P, diluted 1:500) and Ab-4 anti-caspase-3 activated form (Oncogene Research Products, San Diego, Calif.; AM65, diluted 1:200). Second antibodies were goat anti-mouse IgG conjugated with Alexa Fluor 488 (Molecular Probes, Eugene, Oreg.; A11029, diluted 1:200) for tubulin, and Cy3-conjugated affinity purified goat anti-mouse IgG, F (ab')2 fragment specific (Jackson ImmunoResearch Laboratories, West Grove, Pa.; diluted 1:600) for caspase. Mouse monoclonal anti-GFAP-Cy3 conjugate antibody (Sigma-Aldrich; C9205, diluted 1:400) was applied 1 hour at RT. After washing in PBS, coverslips were mounted in Mowiol (Calbiochem, LaJolla, Calif.) and photographed in an Olympus IX-70 FLA microscope with a DVC-1310C digital camera (DVS, Austin, Tex.) and images processed by Photoshop.

The invention claimed is:

1. A method for treating and/or inhibiting Chemotherapy Induced Peripheral Neuropathy (CIPN), comprising administering to a patient in need thereof an effective amount of an IL6R/IL6 chimeric agent which is
   a) a chimera comprising a soluble IL6R moiety and an IL6 moiety, said soluble IL6R moiety comprising the cytokine receptor domain (amino acids 113 to 323 of SEQ ID NO:1) of the extracellular fragment of IL6R (gp80), and said IL6 moiety being a mature human IL6 (amino acids 28 to 212 of SEQ ID NO:2) or a contiguous fragment thereof, said IL6 moiety having IL6R binding activity and IL6R-mediated gp130 binding activity, and said soluble IL6R moiety having gp130-dimerizing activity,
   b) a mutein comprising an amino acid sequence that is
      (i) at least 80% identical to a chimera of (a), (ii) at least 80% identical to a chimera of (a) but that differs from said chimera of (a) solely by
   (a') one or more amino acid, substitutions, and/or
   (b') one or more amino acid insertions or deletions, hut the total number of insertions and deletions is under 30 amino acids,
   c) a derivative of (a) or (b), wherein (a) or (b) is derivatized by one or more derivatizations selected from the group consisting of an aliphatic ester derivative of a carboxyl group, an amide derivative of a carboxyl group, an N-acyl derivative of a free amino group, an O-acyl derivative of a free hydroxyl group, and PEGylation of a functional group of an amino acid residue comprised by said agent, or
   d) a salt of (a), (b), or (C),
   wherein said CIPN is not induced by administration of streptozotocin,
   wherein said agent has gp130 binding and gp130-dimerizing activity, optionally together with a pharmaceutically acceptable carrier,
   wherein at the time of administration of the chimeric agent, the patient is not suffering from diabetic neuropathy.

2. The method according to claim 1, wherein the CIPN is caused by chemotherapy agents selected from the group consisting of cisplatin, dicarbazine, streptozocin, cyclophosphamide, carmustine, lomustine, procarbazine, mitomycin, cytarabine, methotrexate, 5-fluorouracil, vinblastine, vincristine, bleomycin, paclitaxel, asparaginase, busulfan, carboplatin, dacarbazine, fludarabine, hydroxyurea, ifosfamide, mercaptopurine, mitotane, taxol and or a mixture of two or more agents thereof.

3. The method according to claim 2, wherein the chemotherapy agent is vinblastine or vincristine.

4. The method according to claim 1, wherein the chimeric agent is glycosylated at one or more sites.

5. The method according to claim 1, wherein the chimeric agent is non-glycosylated.

6. The method according to claim 1, wherein the agent is a PEGylated derivative.

7. The method according to claim 1, wherein the agent is administered by administering an expression vector comprising the coding sequence of said agent under conditions conducive to expression of said agent in said patient.

8. The method according to claim 7, wherein the vector is a lentiviral vector.

9. A method according to claim 1, wherein the administration is selected from the group consisting of intramuscular, intraperitoneal, intravenous, subcutaneous, and, topical routes.

10. The method of claim 1, wherein said chimeric agent is administered to said patient simultaneously with administration of a chemotherapeutic agent other than streptozotocin.

11. The method according to claim 10, wherein the chemotherapeutic agent is selected from the group consisting of cisplatin, dicarbazine, cyclophosphamide, carmustine, lomustine, procarbazine, mitomycin, cytarabine, methotrexate, 5-fluorouracil, vinblastine, vincristine, bleomycin, paclitaxel, asparaginase, busulfan, carboplatin, dacarbazine, fludarabine, hydroxyurea, ifosfamide, mercaptopurine, mitotane, streptozocin, taxol and a mixture of two or more agents thereof.

12. The method according to claim 11, wherein the chemotherapeutic agent comprises vincristine.

13. The method according to claim 1 wherein the chimeric agent is a fused protein comprising the IL6R/IL6 chimera of (a), or the mutein of (b), fused to an immunoglobulin or fragment thereof, or a derivative according to (c) of such a fused protein, or a salt of said fused protein or derivative thereof.

14. The method according to claim 1 wherein the mutein of (b) is at least 90% identical to a chimera of (a).

15. The method according to claim 1 wherein the chimera of (a) comprises a mature human IL6.

16. The method according to claim 1 wherein the moieties of the chimera of (a) are fused directly to one another.

17. The method according to claim 1 wherein the moieties of the chimera of (a) are connected by a linker amino acid or a linker peptide consisting of not more than 18 amino acids.

18. The method according to claim 1 wherein said mutein of (b) comprises an amino acid sequence that differs from a chimera of (a) solely by one or more amino acid substitutions.

19. The method according to claim 1 wherein said mutein of (b) comprises an amino acid sequence that differs from a chimera of (a) solely by one or more conservative substitutions.

20. The method of claim 1 wherein the chimeric agent is a chimera according to (a) or a derivative according to (c) thereof, or a salt of said chimera or derivative thereof.

21. The method of claim 1 wherein the chimeric agent is a chimera according to (a) or a salt thereof.

22. The method of claim 1 which is a method of treatment.

23. The method of claim 22 wherein the chimeric agent is administered by providing a composition comprising said chimeric agent and administering said composition to the patient.

24. The method of claim 1 wherein the agent is a chimera selected from the group consisting of SEQ ID NOs:3-5, or a derivative according to (c) thereof, or a salt of said chimera or derivative thereof.

25. The method of claim 1 wherein said IL6 moiety is human IL6 or a contiguous fragment thereof that differs from human IL6 by less than 10 amino acid deletions.

26. The method of claim 1 wherein at the time of administration of the chimeric agent, the patient is not suffering from diabetes.

27. The method of claim 1, wherein the differences between said fragment of human IL-6 and mature human IL-6 consist solely of deletion of one or more residues preceding the first alpha helix of mature human IL-6.

28. The method of claim 1, wherein said soluble IL6R moiety comprises amino acids 20-356 of SEQ ID NO:1.

29. The method of claim 28, wherein said agent is a chimera according to (a) or a derivative according to (c) thereof, or a salt of said chimera or derivative.

30. The method of claim 1, wherein said IL-6 moiety comprises amino acids 30-212 of SEQ ID NO:2.

31. The method of claim 30, wherein said agent is a chimera according to (a) or a derivative according to (c) thereof, or a salt of said chimera or derivative.

32. The method of claim 28, wherein said IL-6 moiety comprises amino acids 30-212 of SEQ ID NO:2.

33. The method of claim 32, wherein said agent is a chimera according to (a) or a derivative according to (c) thereof, or a salt of said chimera or derivative.

34. The method of claim 1, wherein the CIPN is induced by a chemotherapeutic agent that is a vinca alkaloid.

35. The method of claim 1, wherein said chimeric agent comprises, as said IL-6 moiety, amino acids 29-212 of SEQ ID NO:2.

36. The method of claim 1, wherein said chimeric agent comprises, as said soluble IL6R moiety, amino acids 20-356 of SEQ ID NO:1.

37. The method of claim 35, wherein said chimeric agent comprises, as said soluble IL6R moiety, amino acids 20-356 of SEQ ID NO:1.

38. The method of claim 37, wherein said soluble IL6R moiety and said IL6 moiety are (aa) fused directly to one another, or (bb) connected by a linker amino acid or a linker peptide consisting of not more than 30 amino acids.

39. The method of claim 1 wherein the soluble IL6R moiety precedes the IL6 moiety.

40. The method of claim 38 wherein the soluble IL6R moiety precedes the IL6 moiety.

41. The method of claim 1 wherein the chimera of (a) is SEQ ID NO:3.

42. The method of claim 41 wherein the mutein of (b) is at least 90% identical to the chimera of (a).

43. A method for increasing the dose of a chemotherapeutic agent comprising
(1) treating and/or inhibiting CIPN by the method of claim 1, and
(2) administering to said patient a dose of a chemotherapeutic agent that is increased relative to a dose of that chemotherapeutic agent given the same patient prior to administration of said chimeric agent, wherein said chemotherapeutic agent is not streptozotocin.

44. In a method of chemotherapy that comprises administration of an amount of a chemotherapeutic agent to a patient in need thereof, the improvement comprising inhibiting or treating peripheral neuropathy inducible or induced by said chemotherapeutic agent by the method of claim 1, whereby the amount of said chemotherapeutic agent administered to said patient is higher than the amount that could be given to said patient without inducing peripheral neuropathy in the absence of said chimeric agent, wherein the chemotherapeutic agent is not streptozotocin.

45. The method of claim 44 wherein the chimeric agent is first administered prior to commencement of chemotherapy.

46. The method of claim 44 wherein the chimeric agent is administered at least once with or after commencement of chemotherapy.

47. The method of claim 1 wherein the chimeric agent is first administered prior to commencement of chemotherapy in a patient in need of chemotherapy, and such administration results in inhibition of chemotherapy-induced peripheral neuropathy in said patient after commencement of chemotherapy.

48. The method of claim 1 wherein the total number of insertions and deletions according to (b)(ii)(b') is under 10 amino acids.

49. The method of claim 23 wherein at the time of administration of the chimeric agent, the patient is not suffering from diabetes.

50. The method of claim 49 wherein the soluble IL6R moiety precedes the IL6 moiety.

51. The method of claim 50 wherein the mutein of (b) is at least 90% identical to a chimera of (a).

52. The method of claim 51 wherein said mutein of (b) comprises an amino acid sequence that differs from a chimera of (a) solely by one or more amino acid substitutions.

53. The method of claim 52, wherein the differences between said fragment of human IL-6 and mature human IL-6 consist solely of deletion of one or more residues preceding the first alpha helix of mature human IL-6.

54. The method of claim 53, wherein said chimeric agent comprises, as said soluble IL6R moiety, amino acids 20-356 of SEQ ID NO:1.

55. The method of claim 52, wherein said chimeric agent comprises, as said IL-6 moiety, amino acids 29-212 of SEQ ID NO:2, and as said soluble IL6R moiety, amino acids 20-356 of SEQ ID NO:1.

56. The method of claim 55, wherein said soluble IL6R moiety and said IL6 moiety are (i) fused directly to one another, or (ii) connected by a linker amino acid or a linker peptide consisting of not more than 30 amino acids.

57. The method of claim 56 wherein the chimeric agent is SEQ ID NO:3, or a derivative according to (c) thereof, or a salt of SEQ ID NO:3 or said derivative.

58. The method of claim 57, wherein said chimeric agent is SEQ ID NO:3 or a salt thereof.

59. The method of claim 58 wherein the chimeric agent is administered to the patient with or after administration of a chemotherapeutic agent comprising a vinca alkaloid.

60. The method of claim 58 wherein the chimeric agent is administered to the patient with or after administration of a chemotherapeutic agent comprising vincristine.

61. The method of claim 38 wherein, if (bb) applies, the linker amino acid or linker peptide is 1-3 amino acids, or is a linker peptide selected from the group consisting of EFGAGLVLGGQFM (SEQ ID NO: 6), GGGGD-PGGGGGGPG (SEQ ID NO:7), RGGGGSGGGGSVE (SEQ ID NO:8), GGGGSGGGGSGGGGS (SEQ ID NO:9), GGGGSGGGGS (amino acids 1-10 of SEQ ID NO:9), GGGGS (amino acids 1-5 of SEQ ID NO:9), and GGGG (amino acids 1-4 of SEQ ID NO:9).

\* \* \* \* \*

SEQUENCE LISTING

```
<160> NUMBER OF SEQ ID NOS: 9

<210> SEQ ID NO 1
<211> LENGTH: 468
<212> TYPE: PRT
<213> ORGANISM: Homo sapiens

<400> SEQUENCE: 1

Met Leu Ala Val Gly Cys Ala Leu Leu Ala Ala Leu Leu Ala Ala Pro
1               5                   10                  15
```

-continued

```
Gly Ala Ala Leu Ala Pro Arg Arg Cys Pro Ala Gln Glu Val Ala Arg
             20                  25                  30
Gly Val Leu Thr Ser Leu Pro Gly Asp Ser Val Thr Leu Thr Cys Pro
         35                  40                  45
Gly Val Glu Pro Glu Asp Asn Ala Thr Val His Trp Val Leu Arg Lys
     50                  55                  60
Pro Ala Ala Gly Ser His Pro Ser Arg Trp Ala Gly Met Gly Arg Arg
65                  70                  75                  80
Leu Leu Leu Arg Ser Val Gln Leu His Asp Ser Gly Asn Tyr Ser Cys
                 85                  90                  95
Tyr Arg Ala Gly Arg Pro Ala Gly Thr Val His Leu Leu Val Asp Val
            100                 105                 110
Pro Pro Glu Glu Pro Gln Leu Ser Cys Phe Arg Lys Ser Pro Leu Ser
        115                 120                 125
Asn Val Val Cys Glu Trp Gly Pro Arg Ser Thr Pro Ser Leu Thr Thr
    130                 135                 140
Lys Ala Val Leu Leu Val Arg Lys Phe Gln Asn Ser Pro Ala Glu Asp
145                 150                 155                 160
Phe Gln Glu Pro Cys Gln Tyr Ser Gln Glu Ser Gln Lys Phe Ser Cys
                165                 170                 175
Gln Leu Ala Val Pro Glu Gly Asp Ser Ser Phe Tyr Ile Val Ser Met
            180                 185                 190
Cys Val Ala Ser Ser Val Gly Ser Lys Phe Ser Lys Thr Gln Thr Phe
        195                 200                 205
Gln Gly Cys Gly Ile Leu Gln Pro Asp Pro Pro Ala Asn Ile Thr Val
    210                 215                 220
Thr Ala Val Ala Arg Asn Pro Arg Trp Leu Ser Val Thr Trp Gln Asp
225                 230                 235                 240
Pro His Ser Trp Asn Ser Ser Phe Tyr Arg Leu Arg Phe Glu Leu Arg
                245                 250                 255
Tyr Arg Ala Glu Arg Ser Lys Thr Phe Thr Thr Trp Met Val Lys Asp
            260                 265                 270
Leu Gln His His Cys Val Ile His Asp Ala Trp Ser Gly Leu Arg His
        275                 280                 285
Val Val Gln Leu Arg Ala Gln Glu Glu Phe Gly Gln Gly Glu Trp Ser
    290                 295                 300
Glu Trp Ser Pro Glu Ala Met Gly Thr Pro Trp Thr Glu Ser Arg Ser
305                 310                 315                 320
Pro Pro Ala Glu Asn Glu Val Ser Thr Pro Met Gln Ala Leu Thr Thr
                325                 330                 335
Asn Lys Asp Asp Asp Asn Ile Leu Phe Arg Asp Ser Ala Asn Ala Thr
            340                 345                 350
Ser Leu Pro Val Gln Asp Ser Ser Val Pro Leu Pro Thr Phe Leu
        355                 360                 365
Val Ala Gly Gly Ser Leu Ala Phe Gly Thr Leu Leu Cys Ile Ala Ile
    370                 375                 380
Val Leu Arg Phe Lys Lys Thr Trp Lys Leu Arg Ala Leu Lys Glu Gly
385                 390                 395                 400
Lys Thr Ser Met His Pro Pro Tyr Ser Leu Gly Gln Leu Val Pro Glu
                405                 410                 415
Arg Pro Arg Pro Thr Pro Val Leu Val Pro Leu Ile Ser Pro Pro Val
            420                 425                 430
Ser Pro Ser Ser Leu Gly Ser Asp Asn Thr Ser Ser His Asn Arg Pro
        435                 440                 445
```

Asp Ala Arg Asp Pro Arg Ser Pro Tyr Asp Ile Ser Asn Thr Asp Tyr
    450                 455                 460

Phe Phe Pro Arg
465

<210> SEQ ID NO 2
<211> LENGTH: 212
<212> TYPE: PRT
<213> ORGANISM: Homo sapiens

<400> SEQUENCE: 2

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
            85                  90                  95

Glu Lys Asp Gly Cys Phe Gln Ser Gly Phe Asn Glu Glu Thr Cys Leu
        100                 105                 110

Val Lys Ile Ile Thr Gly Leu Leu Glu Phe Glu Val Tyr Leu Glu Tyr
    115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 3
<211> LENGTH: 524
<212> TYPE: PRT
<213> ORGANISM: Artificial Sequence
<220> FEATURE:
<223> OTHER INFORMATION: Chebath chimera of portions of human IL-6R
      (20-356 of precursor, 1-337 of mature), and human IL-6 (29-212 of
      precursor, 1-184 of a mature isoform), with 3 aa linker

<400> SEQUENCE: 3

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

```
Arg Ser Val Gln Leu His Asp Ser Gly Asn Tyr Ser Cys Tyr Arg Ala
 65                  70                  75                  80

Gly Arg Pro Ala Gly Thr Val His Leu Leu Val Asp Val Pro Pro Glu
                 85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
                180                 185                 190

Gly Ile Leu Gln Pro Asp Pro Pro Ala Asn Ile Thr Val Thr Ala Val
            195                 200                 205

Ala Arg Asn Pro Arg Trp Leu Ser Val Thr Trp Gln Asp Pro His Ser
210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
                260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Glu Phe Met Pro Val Pro Pro Gly Glu Asp Ser Lys Asp Val Ala
                340                 345                 350

Ala Pro His Arg Gln Pro Leu Thr Ser Ser Glu Arg Ile Asp Lys Gln
            355                 360                 365

Ile Arg Tyr Ile Leu Asp Gly Ile Ser Ala Leu Arg Lys Glu Thr Cys
        370                 375                 380

Asn Lys Ser Asn Met Cys Glu Ser Ser Lys Glu Ala Leu Ala Glu Asn
385                 390                 395                 400

Asn Leu Asn Leu Pro Lys Met Ala Glu Lys Asp Gly Cys Phe Gln Ser
                405                 410                 415

Gly Phe Asn Glu Glu Thr Cys Leu Val Lys Ile Ile Thr Gly Leu Leu
                420                 425                 430

Glu Phe Glu Val Tyr Leu Glu Tyr Leu Gln Asn Arg Phe Glu Ser Ser
        435                 440                 445

Glu Glu Gln Ala Arg Ala Val Gln Met Ser Thr Lys Val Leu Ile Gln
        450                 455                 460

Phe Leu Gln Lys Lys Ala Lys Asn Leu Asp Ala Ile Thr Thr Pro Asp
465                 470                 475                 480

Pro Thr Thr Asn Ala Ser Leu Leu Thr Lys Leu Gln Ala Gln Asn Gln
```

```
                    485                 490                 495
Trp Leu Gln Asp Met Thr Thr His Leu Ile Leu Arg Ser Phe Lys Glu
            500                 505                 510

Phe Leu Gln Ser Ser Leu Arg Ala Leu Arg Gln Met
        515                 520

<210> SEQ ID NO 4
<211> LENGTH: 408
<212> TYPE: PRT
<213> ORGANISM: Artificial Sequence
<220> FEATURE:
<223> OTHER INFORMATION: Fischer chimera of portions of human IL-6R
      (113-323 of precursor, 94-304 of mature) and human IL-6 (29-212 of
      precursor, 1-184 of a mature isoform), with 13 aa  linker

<400> SEQUENCE: 4

Pro Pro Glu Glu Pro Gln Leu Ser Cys Phe Arg Lys Ser Pro Leu Ser
1               5                   10                  15

Asn Val Val Cys Glu Trp Gly Pro Arg Ser Thr Pro Ser Leu Thr Thr
            20                  25                  30

Lys Ala Val Leu Leu Val Arg Lys Phe Gln Asn Ser Pro Ala Glu Asp
        35                  40                  45

Phe Gln Glu Pro Cys Gln Tyr Ser Gln Glu Ser Gln Lys Phe Ser Cys
    50                  55                  60

Gln Leu Ala Val Pro Glu Gly Asp Ser Ser Phe Tyr Ile Val Ser Met
65                  70                  75                  80

Cys Val Ala Ser Ser Val Gly Ser Lys Phe Ser Lys Thr Gln Thr Phe
                85                  90                  95

Gln Gly Cys Gly Ile Leu Gln Pro Asp Pro Pro Ala Asn Ile Thr Val
            100                 105                 110

Thr Ala Val Ala Arg Asn Pro Arg Trp Leu Ser Val Thr Trp Gln Asp
        115                 120                 125

Pro His Ser Trp Asn Ser Ser Phe Tyr Arg Leu Arg Phe Glu Leu Arg
    130                 135                 140

Tyr Arg Ala Glu Arg Ser Lys Thr Phe Thr Thr Trp Met Val Lys Asp
145                 150                 155                 160

Leu Gln His His Cys Val Ile His Asp Ala Trp Ser Gly Leu Arg His
                165                 170                 175

Val Val Gln Leu Arg Ala Gln Glu Glu Phe Gly Gln Gly Glu Trp Ser
            180                 185                 190

Glu Trp Ser Pro Glu Ala Met Gly Thr Pro Trp Thr Glu Ser Arg Ser
        195                 200                 205

Pro Pro Ala Arg Gly Gly Gly Ser Gly Gly Gly Ser Val Glu
    210                 215                 220

Pro Val Pro Pro Gly Glu Asp Ser Lys Asp Val Ala Ala Pro His Arg
225                 230                 235                 240

Gln Pro Leu Thr Ser Ser Glu Arg Ile Asp Lys Gln Ile Arg Tyr Ile
                245                 250                 255

Leu Asp Gly Ile Ser Ala Leu Arg Lys Glu Thr Cys Asn Lys Ser Asn
            260                 265                 270

Met Cys Glu Ser Ser Lys Glu Ala Leu Ala Glu Asn Asn Leu Asn Leu
        275                 280                 285

Pro Lys Met Ala Glu Lys Asp Gly Cys Phe Gln Ser Gly Phe Asn Glu
    290                 295                 300

Glu Thr Cys Leu Val Lys Ile Ile Thr Gly Leu Leu Glu Phe Glu Val
305                 310                 315                 320
```

```
Tyr Leu Glu Tyr Leu Gln Asn Arg Phe Glu Ser Ser Glu Glu Gln Ala
                325                 330                 335

Arg Ala Val Gln Met Ser Thr Lys Val Leu Ile Gln Phe Leu Gln Lys
            340                 345                 350

Lys Ala Lys Asn Leu Asp Ala Ile Thr Thr Pro Asp Pro Thr Thr Asn
        355                 360                 365

Ala Ser Leu Leu Thr Lys Leu Gln Ala Gln Asn Gln Trp Leu Gln Asp
    370                 375                 380

Met Thr Thr His Leu Ile Leu Arg Ser Phe Lys Glu Phe Leu Gln Ser
385                 390                 395                 400

Ser Leu Arg Ala Leu Arg Gln Met
            405

<210> SEQ ID NO 5
<211> LENGTH: 499
<212> TYPE: PRT
<213> ORGANISM: Artificial Sequence
<220> FEATURE:
<223> OTHER INFORMATION: Ekida 333AdeltaA chimera of portions of human
      IL-6R (20-333 of precursor) and human IL-6 (28-212 of precursor,
      1-185 of alternative mature isoform), directly linked

<400> SEQUENCE: 5

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270
```

```
Leu Arg Ala Gln Glu Glu Phe Gly Gln Gly Glu Trp Ser Glu Trp Ser
        275                 280                 285
Pro Glu Ala Met Gly Thr Pro Trp Thr Glu Ser Arg Ser Pro Pro Ala
        290                 295                 300
Glu Asn Glu Val Ser Thr Pro Met Gln Ala Ala Pro Val Pro Pro Gly
305                 310                 315                 320
Glu Asp Ser Lys Asp Val Ala Ala Pro His Arg Gln Pro Leu Thr Ser
                325                 330                 335
Ser Glu Arg Ile Asp Lys Gln Ile Arg Tyr Ile Leu Asp Gly Ile Ser
                340                 345                 350
Ala Leu Arg Lys Glu Thr Cys Asn Lys Ser Asn Met Cys Glu Ser Ser
        355                 360                 365
Lys Glu Ala Leu Ala Glu Asn Asn Leu Asn Leu Pro Lys Met Ala Glu
        370                 375                 380
Lys Asp Gly Cys Phe Gln Ser Gly Phe Asn Glu Glu Thr Cys Leu Val
385                 390                 395                 400
Lys Ile Ile Thr Gly Leu Leu Glu Phe Glu Val Tyr Leu Glu Tyr Leu
                405                 410                 415
Gln Asn Arg Phe Glu Ser Ser Glu Glu Gln Ala Arg Ala Val Gln Met
                420                 425                 430
Ser Thr Lys Val Leu Ile Gln Phe Leu Gln Lys Lys Ala Lys Asn Leu
        435                 440                 445
Asp Ala Ile Thr Thr Pro Asp Pro Thr Thr Asn Ala Ser Leu Leu Thr
        450                 455                 460
Lys Leu Gln Ala Gln Asn Gln Trp Leu Gln Asp Met Thr Thr His Leu
465                 470                 475                 480
Ile Leu Arg Ser Phe Lys Glu Phe Leu Gln Ser Ser Leu Arg Ala Leu
                485                 490                 495
Arg Gln Met

<210> SEQ ID NO 6
<211> LENGTH: 13
<212> TYPE: PRT
<213> ORGANISM: Artificial Sequence
<220> FEATURE:
<223> OTHER INFORMATION: synthetic

<400> SEQUENCE: 6

Glu Phe Gly Ala Gly Leu Val Leu Gly Gly Gln Phe Met
1               5                   10

<210> SEQ ID NO 7
<211> LENGTH: 14
<212> TYPE: PRT
<213> ORGANISM: Artificial Sequence
<220> FEATURE:
<223> OTHER INFORMATION: synthetic

<400> SEQUENCE: 7

Gly Gly Gly Gly Asp Pro Gly Gly Gly Gly Gly Pro Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: synthetic

<400> SEQUENCE: 8
```

```
Arg Gly Gly Gly Gly Ser Gly Gly Gly Ser Val Glu
1               5                   10
```

<210> SEQ ID NO 9
<211> LENGTH: 15
<212> TYPE: PRT
<213> ORGANISM: Artificial Sequence
<220> FEATURE:
<223> OTHER INFORMATION: synthetic

<400> SEQUENCE: 9

```
Gly Gly Gly Gly Ser Gly Gly Gly Gly Ser Gly Gly Gly Gly Ser
1               5                   10                  15
```